(12) United States Patent
Pav (10) Patent No.: US 8,064,975 B2
(45) Date of Patent: Nov. 22, 2011

(54) SYSTEM AND METHOD FOR PROBABILITY BASED DETERMINATION OF ESTIMATED OXYGEN SATURATION

(75) Inventor: Steven E. Pav, San Francisco, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1461 days.

(21) Appl. No.: 11/524,167

(22) Filed: Sep. 20, 2006

(65) Prior Publication Data

US 2008/0076986 A1   Mar. 27, 2008

(51) Int. Cl.
*A61B 5/1455* (2006.01)
(52) U.S. Cl. ......... 600/323; 600/322; 600/324; 600/502
(58) Field of Classification Search ........... 600/309–344
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,911,167 A | 3/1990 | Corenman et al. | |
| 4,936,679 A | 6/1990 | Mersch | |
| 4,972,331 A | 11/1990 | Chance | |
| 5,119,815 A | 6/1992 | Chance | |
| 5,122,974 A | 6/1992 | Chance | |
| 5,167,230 A | 12/1992 | Chance | |
| 5,297,548 A | 3/1994 | Pologe | |
| 5,351,685 A * | 10/1994 | Potratz | 600/330 |
| 5,355,880 A | 10/1994 | Thomas et al. | |
| 5,372,136 A | 12/1994 | Steuer et al. | |
| 5,385,143 A | 1/1995 | Aoyagi | |
| 5,482,036 A | 1/1996 | Diab et al. | |
| 5,553,614 A | 9/1996 | Chance | |
| 5,564,417 A | 10/1996 | Chance | |
| 5,575,285 A | 11/1996 | Takanashi et al. | |
| 5,630,413 A | 5/1997 | Thomas et al. | |
| 5,645,059 A | 7/1997 | Fein et al. | |
| 5,645,060 A | 7/1997 | Yorkey | |
| 5,692,503 A | 12/1997 | Kuenstner | |

(Continued)

FOREIGN PATENT DOCUMENTS

DE   102 13 692 A1   10/2003

(Continued)

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

(Continued)

*Primary Examiner* — Eric Winakur
*Assistant Examiner* — Chu Chuan (JJ) Liu (57) ABSTRACT

Embodiments of the present invention relate to a method of estimating a blood flow characteristic in a patient. Present embodiments include providing a first probability distribution for an actual value of a function of the blood flow characteristic based on a previous value of the function, providing a second probability distribution describing a probability that observations of the blood flow characteristic were made given that the blood flow characteristic took a certain value, and combining the first and second probability distributions to facilitate selection of a most likely value of the function for posting as the value of the estimated blood flow characteristic.

29 Claims, 9 Drawing Sheets

U.S. PATENT DOCUMENTS

| | | | |
|---|---|---|---|
| 5,758,644 A | 6/1998 | Diab et al. | |
| 5,779,631 A | 7/1998 | Chance | |
| 5,830,139 A | 11/1998 | Abreu | |
| 5,842,981 A | 12/1998 | Larsen et al. | |
| 5,873,821 A | 2/1999 | Chance et al. | |
| 5,995,856 A | 11/1999 | Mannheimer et al. | |
| 6,011,986 A | 1/2000 | Diab et al. | |
| 6,064,898 A | 5/2000 | Aldrich | |
| 6,120,460 A | 9/2000 | Abreu | |
| 6,134,460 A | 10/2000 | Chance | |
| 6,163,715 A | 12/2000 | Larsen et al. | |
| 6,181,958 B1 | 1/2001 | Steuer et al. | |
| 6,230,035 B1 | 5/2001 | Aoyagi et al. | |
| 6,266,546 B1 | 7/2001 | Steuer et al. | |
| 6,312,393 B1 | 11/2001 | Abreu | |
| 6,397,091 B2 | 5/2002 | Diab et al. | |
| 6,415,236 B2 | 7/2002 | Kobayashi et al. | |
| 6,438,399 B1 | 8/2002 | Kurth | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,591,122 B2 | 7/2003 | Schmitt | |
| 6,594,512 B2 | 7/2003 | Huang | |
| 6,594,513 B1 | 7/2003 | Jobsis et al. | |
| 6,606,509 B2 | 8/2003 | Schmitt | |
| 6,615,064 B1 | 9/2003 | Aldrich | |
| 6,622,095 B2 | 9/2003 | Kobayashi et al. | |
| 6,636,752 B1 * | 10/2003 | Madarasz et al. | 600/310 |
| 6,658,277 B2 | 12/2003 | Wasserman | |
| 6,662,030 B2 | 12/2003 | Khalil et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,690,958 B1 | 2/2004 | Walker et al. | |
| 6,708,048 B1 | 3/2004 | Chance | |
| 6,711,424 B1 | 3/2004 | Fine et al. | |
| 6,711,425 B1 | 3/2004 | Reuss | |
| 6,785,568 B2 | 8/2004 | Chance | |
| 6,801,797 B2 | 10/2004 | Mannheimer et al. | |
| 6,801,799 B2 | 10/2004 | Mendelson | |
| 6,873,865 B2 | 3/2005 | Steuer et al. | |
| 6,949,081 B1 | 9/2005 | Chance | |
| 6,961,598 B2 | 11/2005 | Diab | |
| 7,027,849 B2 | 4/2006 | Al-Ali | |
| 7,047,055 B2 | 5/2006 | Boas et al. | |
| 7,079,880 B2 | 7/2006 | Stetson | |
| 7,225,013 B2 | 5/2007 | Geva et al. | |
| 7,292,883 B2 | 11/2007 | De Felice et al. | |
| 7,343,187 B2 | 3/2008 | Stetson | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0230106 A1 | 11/2004 | Schmitt et al. | |
| 2005/0080323 A1 | 4/2005 | Kato | |
| 2005/0101850 A1 | 5/2005 | Parker | |
| 2005/0107676 A1 | 5/2005 | Acosta et al. | |
| 2005/0113656 A1 | 5/2005 | Chance | |
| 2005/0168722 A1 | 8/2005 | Forstner et al. | |
| 2005/0192488 A1 | 9/2005 | Bryenton et al. | |
| 2005/0203357 A1 | 9/2005 | Debreczeny et al. | |
| 2005/0267346 A1 | 12/2005 | Faber et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0025931 A1 | 2/2006 | Rosen et al. | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0253007 A1 | 11/2006 | Cheng et al. | |
| 2007/0142719 A1 | 6/2007 | Kawasaki et al. | |

FOREIGN PATENT DOCUMENTS

| | | |
|---|---|---|
| JP | 5-212016 | 8/1993 |
| WO | WO 92/20273 | 11/1992 |
| WO | WO 94/03102 | 2/1994 |
| WO | WO 97/49330 | 12/1997 |
| WO | WO 01/45553 A1 | 6/2001 |

OTHER PUBLICATIONS

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093.

Bongard, Frederic S., et al., "Continuous Dual Oximetry in Surgical critical care—Indications and Limitations," *Annals of Surgery*, vol. 216, No. 1, pp. 60-68 (1992).

Rabiner, Lawrence R., "A Tutorial on Hidden Markov Models and Selected Applications in Speech Recognition," Proceedings of the IEEE, vol. 77, No. 2, Feb. 1989, pp. 257-286.

\* cited by examiner

SYSTEM AND METHOD FOR PROBABILITY BASED DETERMINATION OF ESTIMATED OXYGEN SATURATION

BACKGROUND OF THE INVENTION

1. Field of the Invention

The present invention relates generally to medical devices. More particularly, the present invention relates to estimating blood oxygen saturation in a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Pulse oximetry may be defined as a non-invasive technique that facilitates monitoring of a patient's blood flow characteristics. For example, pulse oximetry may be used to measure blood oxygen saturation of hemoglobin in a patient's arterial blood and/or the patient's heart rate. Specifically, these blood flow characteristic measurements may be acquired using a non-invasive sensor that passes light through a portion of a patient's blood perfused tissue and photoelectrically senses the absorption and scattering of light through the blood perfused tissue. A typical signal resulting from the sensed light may be referred to as a plethysmographic waveform. Once acquired, this measurement of the absorbed and scattered light may be used with various algorithms to estimate an amount of blood constituent in the tissue. It should be noted that the amount of arterial blood in the tissue is time varying during a cardiac cycle, which is reflected in the plethysmographic waveform.

The accuracy of blood flow characteristic estimations obtained via pulse oximetry depends on a number of factors. For example, variations in light absorption characteristics can affect accuracy depending on where (e.g., finger, foot, or ear) the sensor is applied on a patient or depending on the physiology of the patient. Additionally, various types of noise and interference can create inaccuracies. For example, electrical noise, physiological noise, and other interference can contribute to inaccurate blood flow characteristic estimates. Some sources of noise are consistent, predictable, and/or minimal, while some sources of noise are erratic and cause major interruptions in the accuracy of blood flow characteristic measurements. Accordingly, it is desirable to provide a system and method that continues to provide substantially accurate blood flow characteristic measurements during interference and noisy periods as well as during periods with little or no noise.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention relate to providing an estimation of blood oxygen saturation ($SpO_2$) at a particular time or over a designated time period based on a previous $SpO_2$ estimation, related probability estimations, initial $SpO_2$ measurements, and a noise value associated with the readings. Rather than storing or utilizing numerous historical data points to facilitate reducing the effects of noise, in accordance with present embodiments it may be assumed that the blood oxygen saturation value can be predicted based on an immediately prior value of the blood oxygen saturation. Specifically, in accordance with present embodiments, first and second portions of a determination may be combined to establish a probable actual $SpO_2$ value based on a prior $SpO_2$ value and an initial $SpO_2$ measurement. In other words, present embodiments estimate what the actual $SpO_2$ value should be based on a preceding $SpO_2$ value and the value of an initial $SpO_2$ measurement. Once the probable actual $SpO_2$ value is determined, that value may be posted as the calculated value.

Figure 1:
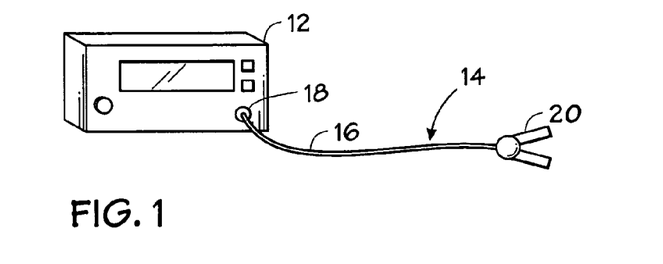
FIG. 1 shows a perspective view of a basic embodiment of a pulse oximeter system in accordance with an exemplary embodiment of the present invention.

FIG. 1 shows a perspective view of an exemplary embodiment of a pulse oximeter system 10. The system 10 includes a pulse oximeter or monitor 12 that communicatively couples to a sensor 14. The sensor 14 may include a sensor cable 16, a connector plug 18, and a body 20 configured to attach to a patient (e.g., patient's finger, ear, forehead, or toe). Pulse oximetry systems such as system 10 may be utilized to observe the oxygenation or oxygen saturation of a patient's arterial blood to estimate the state of oxygen exchange in the patient's body by emitting waves into tissue and detecting the waves after dispersion and/or reflection by the tissue. For example, conventional pulse oximeter systems may emit light from two or more light emitting diodes (LEDs) into pulsatile tissue and then detect the transmitted light with a light detector (e.g., a photodiode or photo-detector) after the light has passed through the pulsatile tissue. The amount of transmitted light that passes through the tissue varies in accordance with the changing amount of blood constituent in the tissue and the related light absorption.

Figure 2:
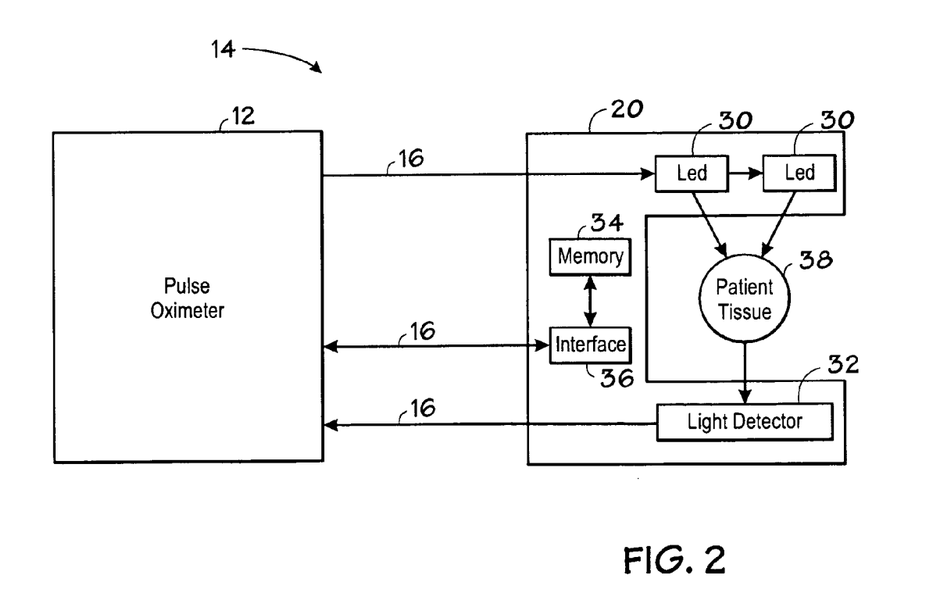
FIG. 2 is a detailed block diagram of the pulse oximeter system of FIG. 1.

Specifically, as illustrated in FIG. 2, the sensor 14 includes two LEDs 30 and a photo-detector 32. The LEDs 30 receive drive signals from the monitor 12 that activate the LEDs 30 and cause them to emit signals alternatively. The sensor 14 is configured such that light from the activated LEDs 30 can pass into a patient's tissue 38. After being transmitted from (or reflected from) the tissue 38, the dispersed light is received by the photo-detector 32. The photo-detector 32 converts the received light into a photocurrent signal, which is then provided to the monitor 12. The illustrated sensor 14 may also include a memory 34 and an interface 36. The memory 34 and/or the monitor 12 may store software applications in accordance with present embodiments. The interface 36 may facilitate communication between the sensor 14 and the monitor 12.

To measure the oxygen saturation of the patient's arterial blood, two different wavelengths of light are typically emitted from the LEDs 30 and are used to calculate the ratio of oxygenated hemoglobin or oxyhemoglobin ($HbO_2$) and deoxygenated hemoglobin or deoxyhemoglobin (Hb), which are dominant hemoglobin components. The light passed through the tissue (e.g., tissue 38) is typically selected to include two or more wavelengths that are absorbed by the blood in an amount related to the amount of blood constituent present in the blood. Specifically, a first wavelength for one of the LEDs 30 is typically selected at a point in the electromagnetic spectrum where the absorption of $HbO_2$ differs from the absorption of reduced Hb. A second wavelength for one of the LEDs 30 is typically selected at a different point in the spectrum where the absorption of Hb and $HbO_2$ differs from those at the first wavelength. For example, LED wavelength selections for measuring normal blood oxygenation levels typically include a red light emitted at approximately 660 nm and an infrared light emitted at approximately 900 nm.

Figure 3:
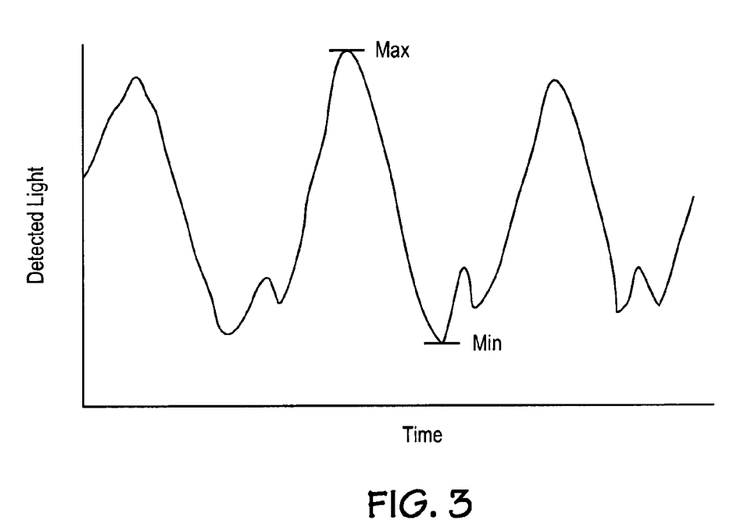
FIG. 3 is a graph of an exemplary plethysmographic waveform which may be generated by the system of FIG. 1.

While various techniques may be utilized to estimate oxygen saturation, in one common technique, the first and second light signals detected by the light detector from red and infrared light sources are conditioned and processed (e.g., via the monitor 12) to determine AC and DC signal components. For example, FIG. 3 illustrates one method of determining AC and DC components from a plethysmographic waveform, wherein maximum (AMX) and minimum (MIN) measurements of each wavelength are measured and correlated as set forth in the following equations:

$$AC = MAX - MIN$$

$$DC = (MAX + MIN)/2. \quad \text{(Eq. 1)}$$

It should be noted that in other embodiments the maximum (MAX) and minimum (MIN) measurements are not necessarily employed to determine the AC and DC components. Indeed, the AC and DC components may be obtained by using essentially any pair of points along both the infrared and red light waveforms.

Once obtained, the AC and DC components may be used to compute a modulation ratio of the red to infrared signals. The modulation ratio is generally referred to as "the ratio of ratios" or Ratrat and may be represented as follows:

$$Ratrat = \frac{AC_{RED}/DC_{RED}}{AC_{IR}/DC_{IR}}. \quad \text{(Eq. 2)}$$

The Ratrat at a particular time K or over a designated timestep K may be represented as follows:

$$Ratrat = \frac{v_K}{u_K}, \quad \text{(Eq. 3)}$$

wherein the variable $v_K$ is representative of a value for red light optical density over timestep K and the variable $u_K$ is representative of a value for infrared light optical density over timestep K. A timestep may include multiple optical observations taken over a designated period of time. For example, a timestep of 1 second may include 53 optical observations, which may be used to determine $v_K$ and $u_K$.

The Ratrat has been observed to correlate well to arterial blood oxygen saturation, as represented by the following equation:

$$Ratrat = f(s), \quad \text{(Eq. 4)}$$

wherein s represents blood oxygen saturation. Pulse oximeters and sensors are typically calibrated empirically by measuring the Ratrat over a range of in vivo measured arterial oxygen saturations ($SaO_2$) on a set of patients (e.g., healthy volunteers). The observed correlation is used in an inverse manner to estimate $SpO_2$ based on the measured value of modulation ratios. A correlation to blood concentrations may be represented by the following equation:

$$\begin{pmatrix} v \\ u \end{pmatrix} = \begin{pmatrix} c_1 & c_{12} \\ c_{21} & c_{22} \end{pmatrix} \begin{pmatrix} OXY \\ DEOXY \end{pmatrix}, \quad \text{(Eq. 5)}$$

wherein the variables $c_{11}$, $c_{12}$, $c_{21}$, and $c_{22}$ represent coefficients, the OXY variable represents an actual value of oxygenated blood concentration, and the DEOXY variable represents an actual value of deoxygenated blood concentration. It should be noted that the coefficients are a function of wavelength. It should further be noted that calculating $SpO_2$ based on the Ratrat is one of various methods that can be utilized to calculate the level of $SpO_2$ in a patient. Indeed, the Ratrat is used herein by way of example, and present embodiments are not limited to the use of the Ratrat in determining $SpO_2$ levels.

Figure 4:
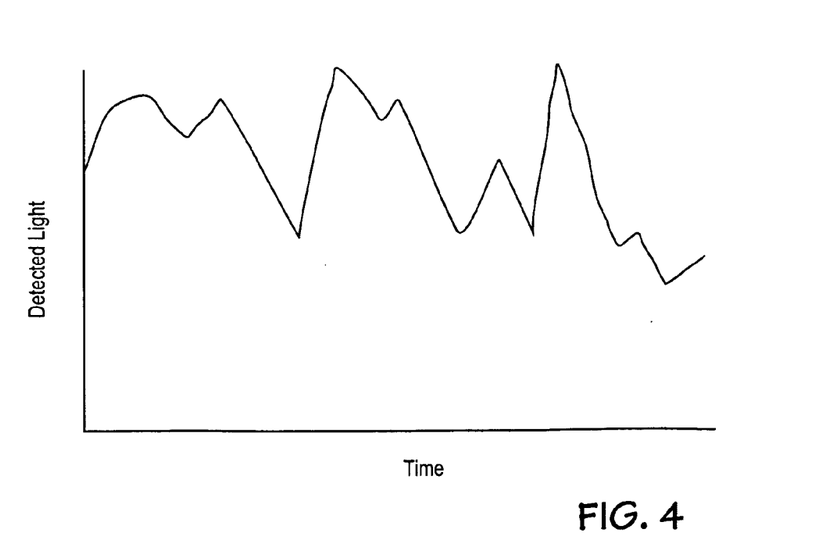
FIG. 4 is a graph of an exemplary plethysmographic waveform, wherein the waveform includes interference due to noise.

The accuracy of blood flow characteristic estimations determined via pulse oximetry can be impacted by various types of noise and interference (e.g., electrical noise, physiological noise, and other interference). In a pulse oximetry system, noise generally manifests as variations in detected light values. Thus, in a noisy system, a "dirty" plethysmographic signal may be obtained. For example, if noise is introduced, the detected light values that define the plethysmographic waveform in FIG. 3 (a "clean" plethysmographic signal) could be extremely skewed, as illustrated by the plethysmographic waveform in FIG. 4 (a "dirty" plethysmographic signal). Such variations in detected light values generally directly impact the calculated value of $SpO_2$. For example, as is clear from the discussion of Ratrat determination above, the value of the Ratrat is dependent on the detected light values, and the Ratrat directly impacts the calculated values of $SpO_2$. Thus, when the Ratrat is used to calculate an $SpO_2$ value, errors in determining the Ratrat due to noise directly impact the calculation of the $SpO_2$ value. Similarly, in other calculations of $SpO_2$, noise can create error in the calculated value of $SpO_2$.

Because noise causes errors such as those discussed above, it is desirable to remove or filter out the effects of noise when determining an $SpO_2$ value with pulse oximetry. Traditional methods for estimating a patient's $SpO_2$ level may limit the impact of noise by utilizing historical data. Indeed, traditional methods may store historical values of $SpO_2$ observed in the patient, and the historical values may then be utilized in calculations to limit the effects of noise. For example, historical values may be averaged (e.g., using ensemble averaging) or trended to facilitate detection and/or filtering of noise or noisy data. Specifically, a current value of the patient's $SpO_2$ level may be estimated based on averaging numerous historical data points and the estimate may then be compared with a measured value to determine whether noise is present. If noise is present, the measured value may be filtered or modified based on the historical data.

Rather than storing or utilizing numerous historical data points to facilitate reducing the effects of noise, in accordance with present embodiments it may be assumed that the value of the $SpO_2$ can be predicted based on an immediately prior value of the $SpO_2$. This can be discussed in terms of the Ratrat because the Ratrat correlates with the value of $SpO_2$. Accordingly, the assumption may be summarized by stating that, in theory, in predicting a future value of the Ratrat (i.e., $Ratrat_{K+1}$) based on knowledge of the most recent Ratrat (i.e., $Ratrat_K$), no additional predictive power can be gained from learning the historical values of the Ratrat (i.e., $Ratrat_0$, $Ratrat_1, \ldots, Ratrat_{K-1}$). For example, the following system may be considered representative:

$$Ratrat = t_K(Ratrat_{K-1})$$

$$v_K = u_K Ratrat_K + n_K^R, \quad \text{(Eq. 6)}$$

wherein $Ratrat_K$ is a function of saturation at major timestep K, $u_K$ is a red optical density at major timestep K, $v_K$ is an infrared optical density at major timestep K, and $n_K^R$ represents observation noise. Observation noise may be defined as noise present in physical observations (e.g., optical or otherwise), and not error in the previous or present estimate of saturation. The function t represents the transition of the Ratrat from one timestep to the next, which includes a random variable. The inclusion of a random variable indicates that given the Ratrat at a previous time interval (i.e., $Ratrat_K$), the value of the Ratrat at a next time interval (i.e., $Ratrat_{K+1}$) can be predicted or estimated, but not necessarily directly calculated.

Embodiments of the present invention assume that $SpO_2$ (and hence Ratrat) follow a Hidden Markov Model of a given distribution. A Hidden Markov Model is a statistical model wherein the system being modeled is assumed to be a Markov process with unknown parameters. A Markov Model or Markov Chain may be characterized by the following property: $P\{X_{k+1}=x|X_k, X_{k-1}, \ldots, X_0\} = P\{X_{k+1}=x|X_k\}$. Only the most recent value of the random variable is relevant for predicting the next value. In some embodiments, the model may be further restricted such that it only takes values in a certain range, or in a certain finite set of numbers. For example, under further restriction the following is representative: $P\{X_{k+1}=x|X_k\}=0$ when x is not a number in that certain range, or in that certain finite set. It should be noted that in some embodiments, there is no need to restrict the Markov process to a finite range. However, it may be assumed that the range is bounded between 0 and 100%, but may take any value in that range. The objective of Viterbi's algorithm is to determine the hidden parameters from observable parameters. The Hidden Markov Model models the underlying process, which is observed with some level of uncertainty (e.g., via optical measurements).

In accordance with present embodiments, first and second portions of a determination may be combined to establish a probable actual $SpO_2$ value based on a prior $SpO_2$ value and an initial $SpO_2$ measurement. In other words, present embodiments estimate what the actual $SpO_2$ value should be based on a preceding $SpO_2$ value and the value of an initial $SpO_2$ measurement. Once the probable actual $SpO_2$ value is determined, that value may be posted as the calculated value. Specifically, in the first portion of the determination, an immediately prior calculated or measured $SpO_2$ value may be utilized to determine a set of predictive paths and potential $SpO_2$ values. These predictive paths and potential $SpO_2$ values correspond to what will probably be the next actual $SpO_2$ value. For example, there is generally a high probability that the $SpO_2$ value following the immediately preceding value will be equivalent to the immediately preceding value. In the second portion of the determination, a set of predictive paths and potential $SpO_2$ values may be determined based on a current $SpO_2$ measurement value. For example, an initial $SpO_2$ measurement may be utilized to determine probabilities associated with potential $SpO_2$ values for the actual $SpO_2$ value. As suggested above, once probabilities based on the immediately preceding $SpO_2$ value and the initial $SpO_2$ measurement are established, they may be combined to predict the actual current $SpO_2$ value for posting. This procedure is discussed in further detail below.

Figure 5:
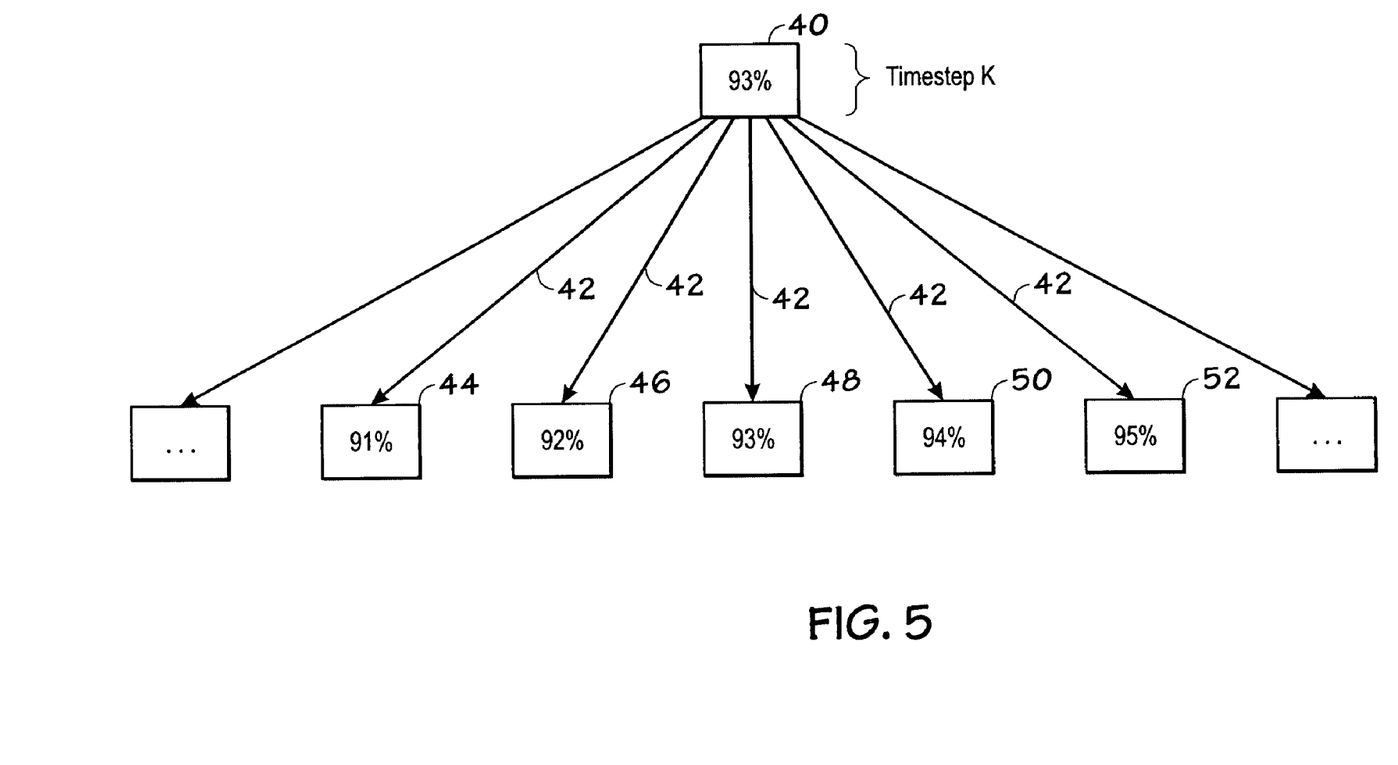
FIG. 5 is a diagram representing predictive paths and potential $SpO_2$ values based on a previous $SpO_2$ reading in accordance with an exemplary embodiment of the present invention.

FIG. 5 is a block diagram representing an example of predictive paths and potential $SpO_2$ values for a current reading that may be determined based on a previously calculated or measured $SpO_2$ value. It should be noted that the predictive paths are not necessarily explicitly constructed in accordance with present embodiments. In other words, the transition illustrated in FIG. 5 may be described as a continuum that does not utilize a discrete list of values. Essentially, the predictive paths and potential $SpO_2$ values represent a probability distribution (e.g., Markov Model transition probability distribution) of what the next $SpO_2$ value is likely to be based solely on the most recently measured and/or determined $SpO_2$ value. This probability distribution may represent what can be referred to as a probability distribution of transition.

Calculating these predictive paths and potential $SpO_2$ values represented in FIG. 5 may be considered the first portion of the procedure for determining the $SpO_2$ value to post as the current value. Accordingly, FIG. 5 may be representative of results from the first portion of the procedure. Specifically, FIG. 5 includes a previous $SpO_2$ measurement or determination (block 40) having an exemplary value of 93%. Block 40 represents the $SpO_2$ value obtained from the Ratrat corresponding to timestep K, wherein K is the most recent previous timestep. Each of the arrows 42 extending from block 40 represents a probability that the value of $SpO_2$ for the current or next timestep (e.g., K+1 or the value of $SpO_2$ for the timestep after that represented by block 40) will correspond to one of the values in the corresponding blocks 44, 46, 48, 50, and 52. In other words, the arrows 42 represent predictive paths for the potential $SpO_2$ values in blocks 44-52. It should be noted that while blocks 44-52 represent a specific range of values, in other embodiments the range and values may be different. Indeed, in some embodiments, the range and values represented by blocks 44-52 may be dependent on a selected model of how saturation can change.

The continuum of probability values is represented by a probability distribution function. As indicated above, blocks 44, 46, 48, 50, and 52 are representative of potential SpO$_2$ values that could be obtained at the next timestep (i.e., K+1) using the corresponding Ratrat for that timestep (i.e., Ratrat$_{K+1}$). These potential values (block 44-52) represent a range of potential SpO$_2$ values based on established relationships between the value of the timestep between K and K+1 (e.g., 1 second) and the initial or immediately preceding SpO$_2$ value (e.g., block 40). The following equation is representative of the relationship between block 40 and blocks 44-52:

$$p(x)=CPr\{\text{Ratrat}_K=\text{Ratrat}_{K-1}+x|\text{Ratrat}_{K-1}\}, \quad \text{(Eq. 7)}$$

wherein C represent a constant that can be ignored and the function Pr{a|b} means "the probability that a occurs conditioned on the fact that b was observed to occur." It may be assumed that a probability distribution function of the transition function t can be estimated by a particular equation or model. In the case of a continuum, the function p(x) is a probability density, which is integrated to obtain probabilities.

The most likely value for SpO$_2$ that will be obtained in the imminent timestep (i.e., K+1) based on the known Ratrat (i.e., Ratrat$_K$) is represented by block 48, which has the same SpO$_2$ value as that of the previous timestep (block 40). Values for the SpO$_2$ at K+1 that have lesser probabilities of occurrence are dispersed outwardly according to a probability distribution function used to determine the probabilities 42 for each potential value (blocks 44-52). For example, in accordance with some embodiments, a piecewise linear spline, a double exponential function, or Gausian probability density function may be utilized to determine probabilities (e.g., probabilities 42). Such probabilities 42 may indicate that, for example, if the timestep is approximately one second, it is highly unlikely that during the transition from K to K+1 the SpO$_2$ level will drop by a certain amount (e.g., twenty points) and that it is highly likely that the SpO$_2$ value will remain the same. Accordingly, changes within a certain range will be given a higher probability value. Generally, these probability values are lower the further the corresponding SpO$_2$ value (blocks 44-52) is from the initial value (block 40) (e.g., the probability of the SpO$_2$ value for timestep K+1 remaining at 93% is greater than that of it changing to 91%) because changes in SpO$_2$ do not typically include large, sudden swings. It should be noted that it may be slightly more likely to have a large increase in the SpO$_2$ value in certain situations (e.g., an oxygen starved patient receiving oxygen).

In accordance with some embodiments, the mean of the probability distribution function for the saturation transition should be the previous value of SpO$_2$. In other words, the probability distribution function of the saturation transition may be designed such that saturation is a Martingale. This generally prevents present embodiments from predicting large fluctuations in saturation levels when presented with noiseless optical observations. Moreover, for this reason, it may be desirable to adjust or tune the probability distribution function such that its variance is minimized, or otherwise controlled. In some embodiments, the probability density function of the saturation transition is represented by a spline function (i.e., a function composed of portions of polynomials linked together). For example, a spline function utilized in accordance with present embodiments may include a piecewise linear function.

Figure 6:
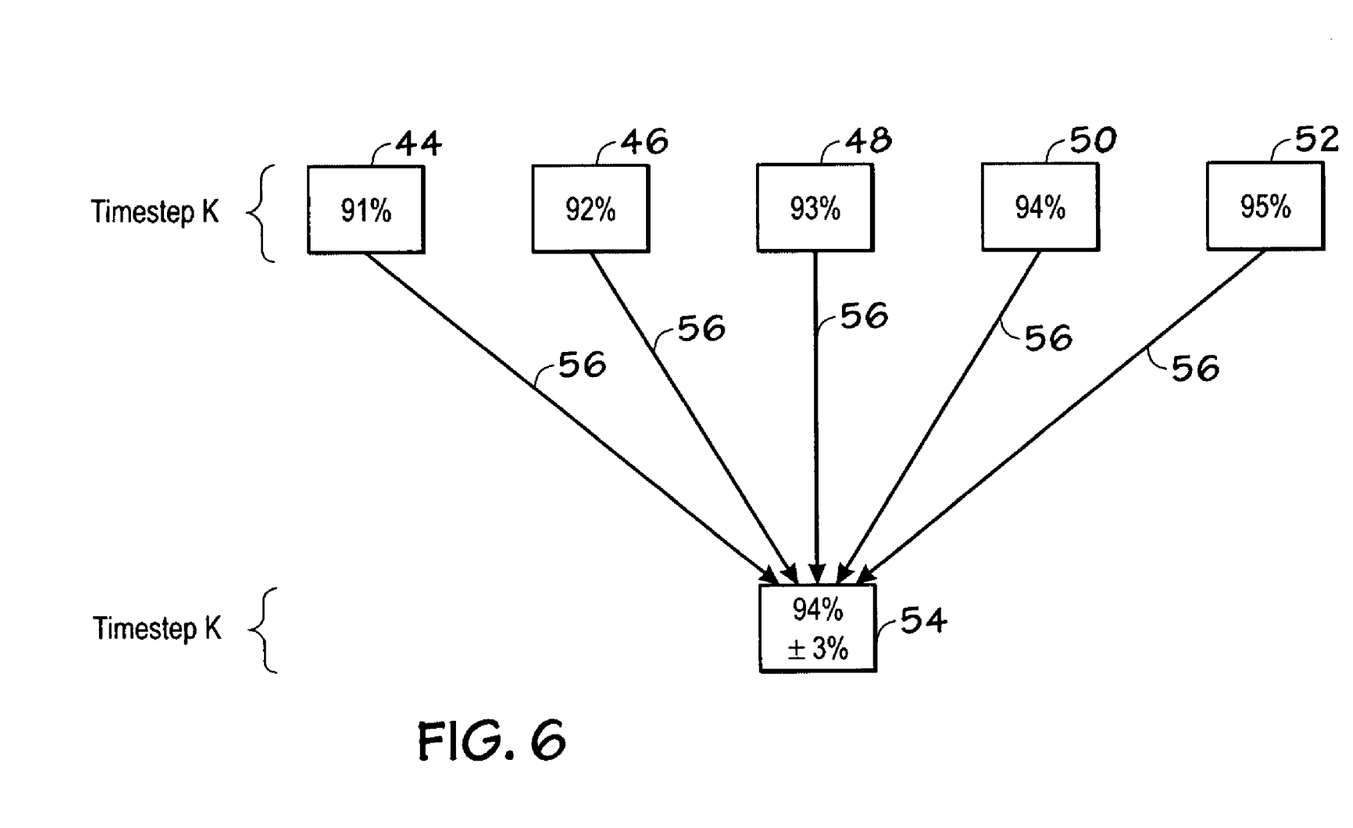
FIG. 6 is a diagram representing predictive paths and the potential $SpO_2$ values for the related timestep based on an initial $SpO_2$ reading for the current timestep in accordance with an exemplary embodiment of the present invention.

FIG. 6 may be representative of results from the second portion of the procedure for determining the SpO$_2$ value to be posted as current. As set forth above, these results may be combined with the results illustrated in FIG. 5 to provide the current SpO$_2$ reading. Specifically, FIG. 6 is a block diagram representing predictive paths and the potential SpO$_2$ values for the related timestep based on an initial SpO$_2$ reading for the current timestep in accordance with embodiments of the present invention. Essentially, the predictive paths and potential SpO$_2$ values represent a probability distribution of what the next SpO$_2$ value is likely to be based on an initial measurement. This probability distribution may represent what can be referred to as a probability distribution of measured values or the probability of observing a given measured value.

Specifically, FIG. 6 includes block 54, which represents an SpO$_2$ value (e.g., 94%±3%) for the current timestep that takes into account observational information. Additionally, FIG. 6 includes the blocks 44, 46, 48, 50, and 52, which are representative of potential actual SpO$_2$ values that could be obtained for the current time step within a certain likelihood. Arrows 56, which connect the potential SpO$_2$ values (blocks 44-52) with the value accounting for observational information (block 54), are representative of probabilities that given the SpO$_2$ value is actually a certain value, the (optical) measurements indicate the given SpO$_2$ value. For example, the probability along the arrow 56 from block 46 to block 54 represents the probability that, given that the SpO$_2$ is actually 92%, optical observations indicate that the SpO$_2$ is 94%. However, the procedure is more general that this example. Optical measurements include an estimate of noise (e.g., ±3%). This estimate of noise facilitates construction of the arrows 56. When the error is small (e.g., ±0.5%), it is likely that SpO$_2$ really is the value indicated by the optical observations (e.g., the probability that the underlying SpO$_2$ is 94% and was observed to be 94% is high, while the probability that the underlying SpO$_2$ value is 92% and was observed to be 94% is low). When the error is larger (e.g., ±6%), the distribution flattens out. In other words, the probabilities associated with the arrows 56 become nearly equal when the error is large. The probabilities 56 may be represented and determined by designated equations, which will be discussed in further detail below.

Figure 7:
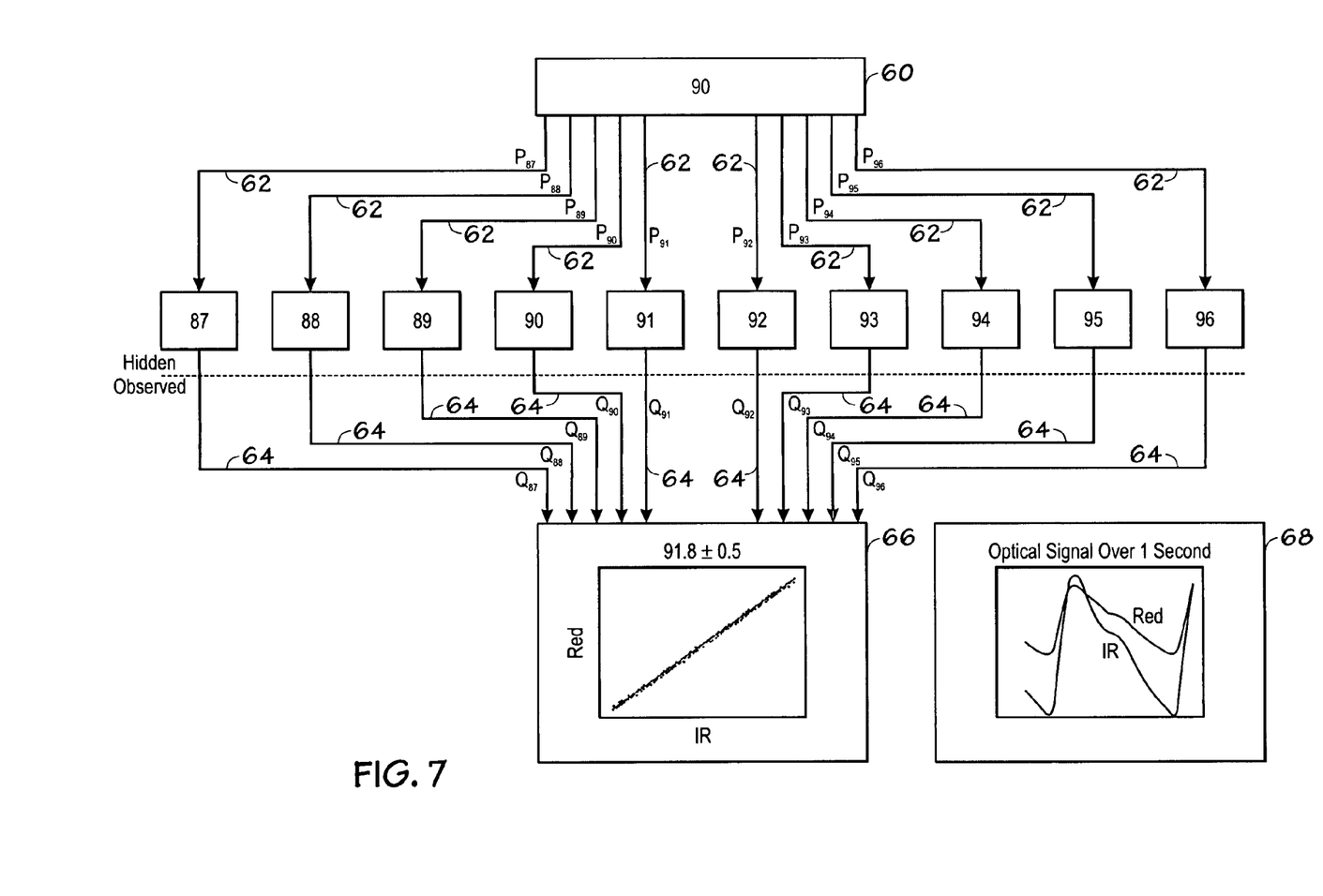
FIG. 7 is a flow diagram of an algorithm employing probability density functions in accordance with an embodiment of the present disclosure.

As illustrated in FIG. 7, once determined, the probabilities represented by arrows 56 may be combined with the probabilities represented by arrows 42 to determine which potential SpO$_2$ value should be posted as the meaningful SpO$_2$ value. The algorithm represented by FIG. 7 employs probability density functions. It should be noted that a probability density function may be defined as the function, f(x), such that given a random variable X, the following equations applies:

$$P(a \leq x \leq b) = \int_a^b f(x)\,dx. \quad \text{(Eq. 8)}$$

Further, it should be noted that, in present embodiments, the probability density function may only need to be known up to a constant.

Determining the meaningful SpO$_2$ value for posting may include the following procedures: let P(x) be a nonzero constant times the probability density function associated with the Hidden Markov Model (i.e. the transition of SpO$_2$ values), let Q(x) be a nonzero constant times the probability density function associated with the observation, and let W(x)=P(x) Q(x) be some constant times the probability density function of the value of SpO₂ at the current state, conditional on the (optical) observations. This may be represented as follows:

$$P(a \leq X_{k+1} \leq b | X_k \text{ known, optical observations}) = D \int_a^b W(x) dx, \quad \text{(Eq. 9)}$$

where D is an unknown constant. Viterbi's algorithm, which is a maximum likelihood estimate algorithm, estimates $X_{k+1}$ by that value x which maximizes W(x). Because P(x) and Q(x) are represented in the algorithm as functions (e.g., P(x) is a linear spline, or the probability distribution function of a Gaussian or normal, double exponential, and so forth, and Q(x) is the probability density function of a Gaussian), this maximum can be found using calculus, and not by checking every value between values (e.g., between 91% and 95%).

In the exemplary embodiment illustrated in FIG. 7, block 60 represents a best estimate of saturation at timestep K based on the previous optical observations. Probabilities 62 ($P_j$) may be based on the Hidden Markov Model of human physiology. Accordingly, these probabilities 62 may only depend on the estimate of saturation, and not on current optical observations. The probabilities 64 ($Q_j$) may be based on a model of optical noise and optical observations since timestep K. The probabilities 64 represent the probability that, if the saturation were j at timestep K+1, the observations would correspond to the observations made. Block 66 represents a linear regression of red to infrared optical signals over the major time step. Block 68 represents the red to infrared optical signals over one second.

When the noise in optical observations is assumed to be independent identically distributed normal random variables with zero mean and a given variance, the least squares regression slope is a random variable whose expected value is the underlying Ratrat with a certain variance. In this case, the value of the probabilities 64 may be generated from the probability distribution function of the normal. In a specific example, if the saturation value is assumed to be 90 at timestep K, and optical observations indicate 91.8±0.5 saturation, the probability that saturation is j at timestep K+1 is $P_j Q_j$, under assumptions of independence. Thus, saturation at K+1 may be estimated by that j and an iterative procedure with future optical observations may be invoked.

Figure 8:
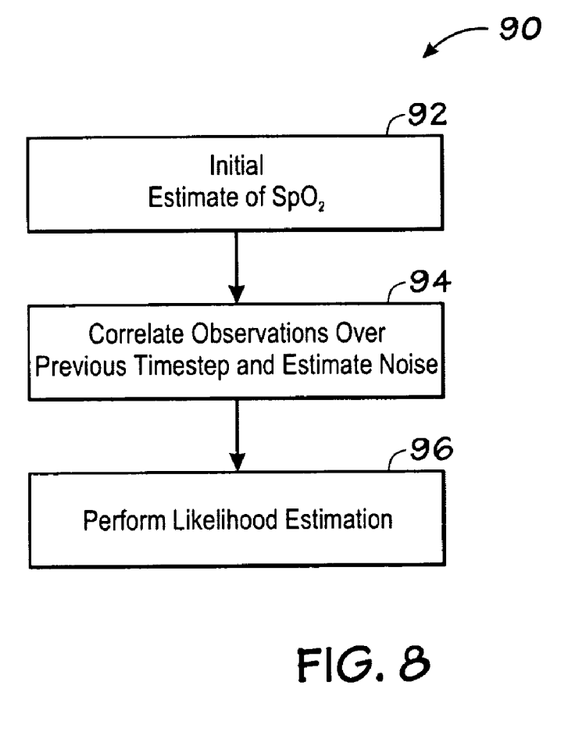
FIG. 8 is a flow diagram of an algorithm for determining an appropriate value to post for a patient's $SpO_2$ level in accordance with an exemplary embodiment of the present disclosure.

FIG. 8 is a block diagram of an algorithm for determining the best value to post for a patient's SpO₂ value based on the value of the Ratrat (i.e., $Ratrat_{K-1}$) for the previous timestep, the current measurement or measurements for the SpO₂ value, the probabilities 42 and 56 relating to the actual occurrence of the SpO₂ value, and estimated noise. The algorithm is generally referred to by reference number 90. Specifically, algorithm 90 includes several steps for determining an appropriate estimate of the Ratrat for timestep K+1 that is substantially accurate during periods of noise and/or interference. The determination of algorithm 90 is largely based on observations during timestep K+1 and a provided (e.g., measured) value of the Ratrat for timestep K. It should be noted that it is assumed in accordance with present embodiments that the sampling rate of optical observations is higher than the meaningful posting rate. For example, in one embodiment optical observations are made at 53 Hz and saturation values are posted at 1 Hz. Intervals between posts may be referred to as timesteps and intervals between observations may be referred to as minor timesteps.

In block 92, an initial estimate of the Ratrat at an initial time or for an initial timestep (i.e., $Ratrat_0$) is provided. This initial value may simply include the value of the Ratrat assigned to the timestep prior to the timestep for which the Ratrat (or the SpO₂ value for posting) is being determined. The initial estimate of the Ratrat may be obtained using various procedures, such as bootstrapping a value from an initial reading. For example, the first estimate of saturation may be the value of the current physical measurement. In other embodiments, an overall probability distribution of the saturation in humans may be determined and utilized as the transition distribution from an unknown saturation in the previous time step. For example, population studies may provide estimates of saturation in groups of people, which may be utilized with safety factors (e.g., lower saturation levels for certain groups and generally lower saturation level estimates) to provide an initial estimate. This universal distribution approach does not require that the previous saturation estimate be known. In another embodiment, an estimate of saturation level and an estimate of confidence in the saturation level may be maintained. For example, information such as "at time step k saturation is in the range of 94.5%-95.499% (posting 94) with 75% certainty" may be maintained. In order to boot strap, the information may be initialized as "at time step 1, the saturation is in the range 89.5%-90.499% (or values provided in accordance with the physical measurement) with 1% certainty (or a value obtained from the physical measurement)."

After establishing the initial estimate, in block 94, the optical observations over the previous timestep are correlated and a noise estimate is obtained. Various procedures may be utilized to provide this noise estimate. For example, block 94 may include performing a linear regression of all the optical observations over the previous timestep to obtain a best fit slope, which may be referred to by the variable $\hat{m}$. Additionally, an estimate of noise may be obtained by determining a sample standard deviation of the residuals, which may be referenced by the variable θ. Under the assumption of normal noise, $\hat{m}$ is distributed as the true slope plus an unbiased normal random variable with variance. This variance may be represented as $\theta^2/\sigma^2_{ir}$, where $\sigma^2_{ir}$ represents the sample standard deviation of the infrared values over the previous timestep. The following equation is representative:

$$\hat{m} = \sigma_k + N\left(0, \frac{\theta^2}{\sigma_x^2}\right) \quad \text{(Eq. 10)}$$

One component of algorithm 90 is the incorporation of a maximum likelihood estimator. That is, the estimate of $Ratrat_K$ is that which is most likely given the previous estimate and the optical evidence over the previous major timestep K−1. This maximum likelihood estimation is represented by block 96, wherein:

$$\overline{Ratrat_j} \leftarrow \overline{Ratrat_{j-1}} + \xi \quad \text{(Eq. 11)}$$

and wherein ξ maximizes the following function:

$$p(\xi)e\left(\frac{-0.5(\hat{m} - Ratrat_{j-1} - \xi)^2}{\frac{\theta^2}{\sigma_{ir}^2}}\right) \quad \text{(Eq. 12)}$$

which is proportional to:

$$Pr\{Ratrat_j - Ratrat_{j-1} = \xi | \overline{Ratrat_{j-1}} = Ratrat_{j-1}\} \quad \text{(Eq. 13)}$$
$$Pr\{\hat{m} \text{ observed} | \hat{m} \sim N(Ratrat_{j-1} + \xi, \theta^2 / \sigma_{ir}^2)\}$$

which represents combining (e.g., essentially multiplying) the probability 42 represented in FIG. 5 with the probability 56 represented in FIG. 6 to determine a posting value based on which of the potential values has the highest probability. Because this is a maximum likelihood calculation, it is unnecessary to compute the cumulative distribution function of the normal, and p(x) can be known only up to a constant. Thus, the value posted as the meaningful $SpO_2$ value is represented by Eq. 13.

Figure 9:
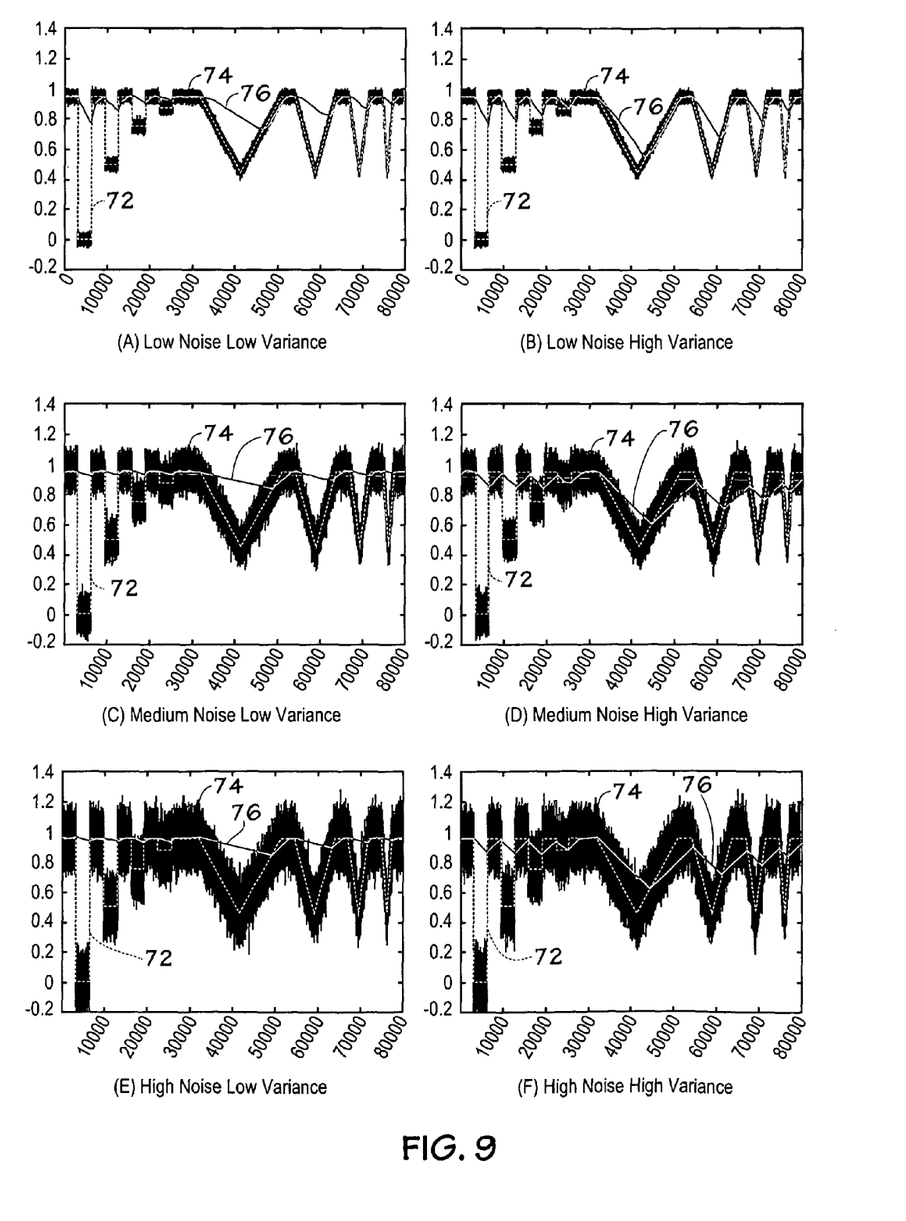
FIGS. 9, 10, and 11 are representations of data acquired by implementing and testing present embodiments against synthetic data using Viterbi's algorithm in accordance with an exemplary embodiment of the present invention.
Figure 10:
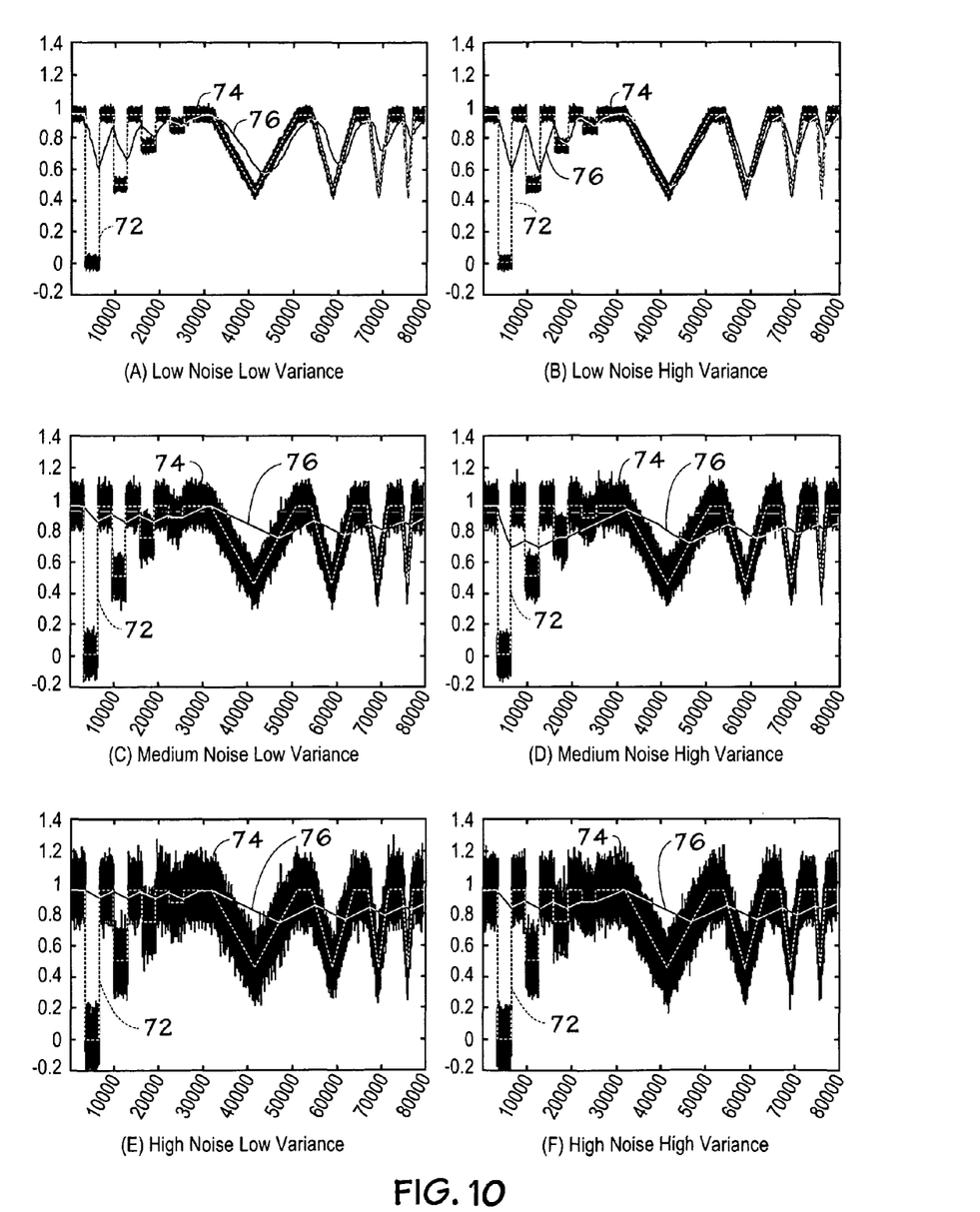
Figure 11:
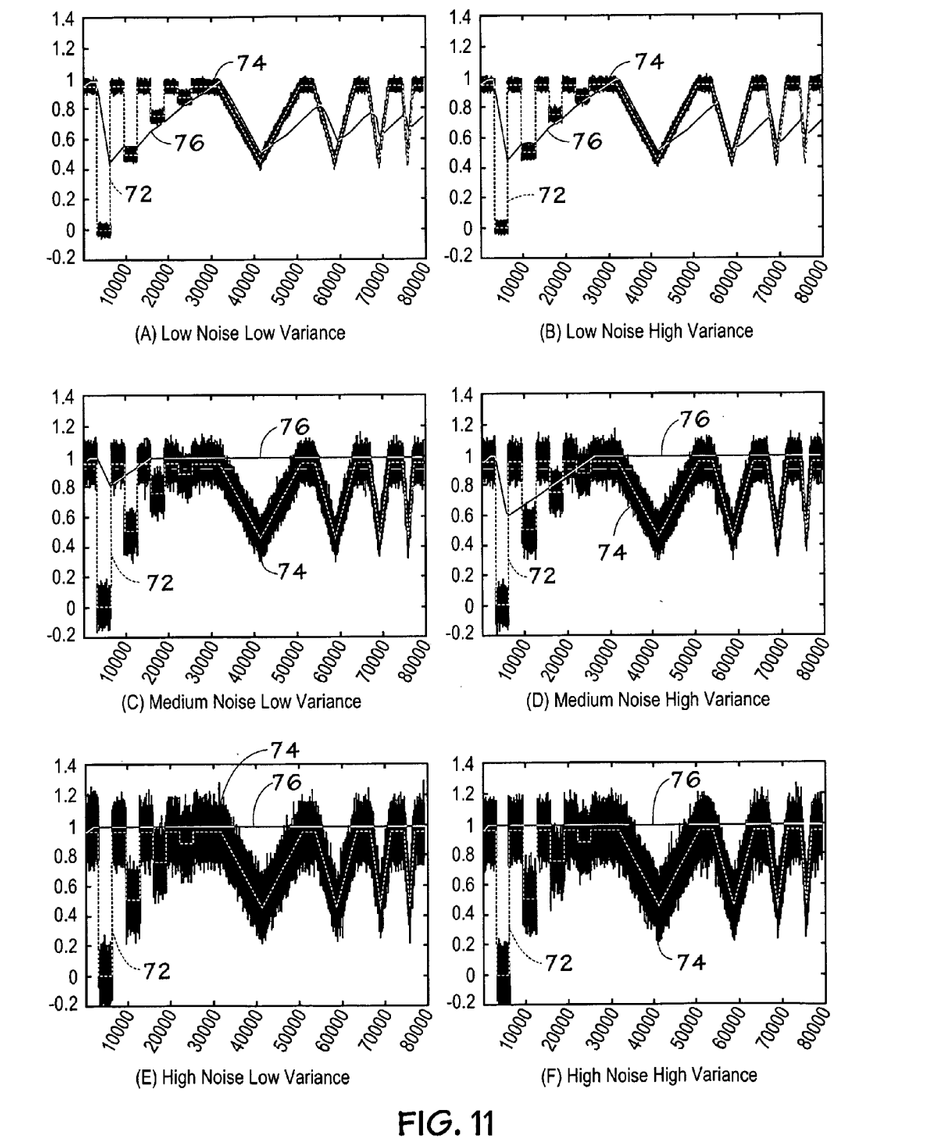

FIGS. 9, 10 and 11 are representations of data acquired by implementing and testing present embodiments against synthetic data using Viterbi's algorithm. The synthetic data consist of a time signal of saturation with a constant level of noise added. The results are plotted in several graphs in each of FIGS. 9, 10, and 11. The different graphs correspond to different levels of noise in the observation, different choices of the variance in the underlying Markov Model, and different choices of the transition limits (up and down) of the Markov Model. Each of FIGS. 9, 10, and 11 include a first graph (A) with low noise and low variance, a second graph (B) with low noise and high variance, a third graph (C) with medium noise and low variance, a fourth graph (D) with medium noise and high variance, a fifth graph (E) with high noise and low variance, and a sixth graph (F) with high noise and high variance. Further, each graph shows an actual underlying synthetic saturation signal 72, observed saturation with noise added 74, and a maximum likelihood estimator (i.e., output of the algorithm) 76.

FIGS. 9, 10, and 11 each illustrate slightly different information. The graphs in FIG. 9 show a model wherein the maximal decrease in saturation transition of the Markov Model is one-third the maximal increase in saturation transition. Specifically, the graphs in FIG. 9 illustrate the results of a maximum likelihood estimation using a Markov Model with a saturation increase allowed at triple the rate of saturation decrease. This approximates physiological reality, as saturation decreases are typically slow, while increases occur quickly with inspiration. The graphs in FIG. 10 show a model wherein the maximal decrease and maximal increase in saturation transition are equal. Specifically, the graphs in FIG. 10 show the results of a maximum likelihood estimation using a Markov Model with saturation increase allowed at the same rate of decrease. The graphs in FIG. 11 show a model wherein the maximal decrease is 4.5 times greater than the maximal increase in saturation transition. Specifically, FIG. 11 shows the results of a maximum likelihood estimation using a Markov Model with the aforementioned ratio between saturation increase and decrease.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of estimating a blood flow characteristic in a patient, comprising:
   providing a first probability distribution for an actual value of a function of the blood flow characteristic based on a previous value of the function;
   providing a second probability distribution describing a probability that observations of the blood flow characteristic were made given that the blood flow characteristic took a certain value; and
   combining the first and second probability distributions to facilitate selection of a most likely value of the function for posting as the value of the estimated blood flow characteristic.

2. The method of claim 1, wherein the blood flow characteristic comprises blood oxygen saturation.

3. The method of claim 1, comprising emitting and detecting first and second wavelengths of light with a sensor, wherein the function is a ratio of ratios based on optical observations of the first and second wavelengths of light.

4. The method of claim 1, comprising maximizing a given equation to facilitate selection of the most likely value of the function.

5. The method of claim 1, comprising determining a noise estimate based on an assumption of normal noise.

6. The method of claim 1, comprising linearly regressing a plurality of optical observations used to determine the previous value and performing a sample standard deviation of residuals to facilitate provision of a noise estimate.

7. The method of claim 1, wherein the previous value is a single blood oxygen saturation estimate.

8. The method of claim 1, comprising providing probabilities for a plurality of potential actual values based on a measured value of the blood flow characteristic and a noise estimate.

9. The method of claim 1, comprising providing probabilities for a plurality of potential actual values based on the previous value of the function.

10. The method of claim 1, comprising:
    emitting light at first and second wavelengths; and
    detecting the light.

11. The method of claim 10, comprising emitting the light at a third wavelength.

12. The method of claim 10, comprising determining an initial value for the function of the blood flow characteristic based solely on the detected light.

13. A method of estimating a blood flow characteristic in a patient, comprising:
    determining a probability distribution of transition for the blood flow characteristic based on a single previous value of the blood flow characteristic;
    calculating a new value for the blood flow characteristic;
    determining a probability distribution of observation describing a probability that observations of the blood flow characteristic were made given that the blood flow characteristic took a certain value; and
    combining the probability distribution of transition and the probability distribution of observation to facilitate selection of a probable value of the blood flow characteristic.

14. The method of claim 13, comprising selecting and posting the probable value as the estimated blood flow characteristic.

15. The method of claim 13, wherein the blood flow characteristic comprises blood oxygen saturation.

16. The method of claim 13, comprising maximizing a given equation to facilitate selection of the probable value of the blood flow characteristic.

17. The method of claim 13, comprising determining a noise estimate based on an assumption of normal noise.

18. The method of claim 13, comprising linearly regressing a plurality of optical observations used to determine the single previous value and performing a sample standard deviation of residuals to facilitate provision of a noise estimate.

19. The method of claim 13, comprising correlating a patient type to a patient blood flow characteristic estimate to provide the single previous value for the blood flow characteristic.

20. The method of claim 13, wherein the single previous value is a single blood oxygen saturation estimate.

21. The method of claim 13, comprising:
emitting light at two or more wavelengths; and
detecting the light.

22. An apparatus for estimating a blood flow characteristic in a patient, comprising:
a sensor configured to facilitate establishment of a measured value of the blood flow characteristic;
a first probability distribution component configured to provide a first probability distribution for an actual value of a function of the blood flow characteristic based on a previous value of the function;
a second probability distribution component configured to provide a second probability distribution describing a probability that observations of the blood flow characteristic were made given that the blood flow characteristic took a certain value; and
a combining component configured to combine the first and second probability distributions to facilitate selection of a most likely value of the function for posting as the value of the estimated blood flow characteristic.

23. The apparatus of claim 22, wherein the function is a ratio of ratios based on optical observations of first and second wavelengths of light utilized by the sensor to facilitate establishment of the measured value of the blood flow characteristic.

24. The apparatus of claim 22, comprising a maximization component configured to maximize a given equation to facilitate selection of the most likely value of the function.

25. The method of claim 22, comprising a regression component configured to linearly regress a plurality of optical observations used to determine the previous value and perform a sample standard deviation of residuals to facilitate provision of a noise estimate.

26. The apparatus of claim 22, comprising:
a first emitter configured to emit light at a first wavelength;
a second emitter configured to emit light at a second wavelength; and
a detector configure to detect the light.

27. The apparatus of claim 26, comprising an estimating component configured to determine an initial value for the function of the blood flow characteristic based solely on the detected light.

28. A method of estimating a blood flow characteristic in a patient, comprising:
providing a first probability distribution for an actual value of a function of the blood flow characteristic based on a previous value of the function, wherein the first probability distribution is a Markov Model transition probability;
providing a second probability distribution describing a probability that observations of the blood flow characteristic were made given that the blood flow characteristic took a certain value; and
combining the first and second probability distributions to facilitate selection of a most likely value of the function for posting as the value of the estimated blood flow characteristic.

29. A method of estimating a blood flow characteristic in a patient, comprising:
providing a first probability distribution for an actual value of a function of the blood flow characteristic based on a previous value of the function;
providing a second probability distribution describing a probability that observations of the blood flow characteristic were made given that the blood flow characteristic took a certain value, wherein the second probability distribution is a linear spline measured value distribution; and
combining the first and second probability distributions to facilitate selection of a most likely value of the function for posting as the value of the estimated blood flow characteristic.

* * * * *